US008815806B2

(12) United States Patent
Aluko et al.

(10) Patent No.: US 8,815,806 B2
(45) Date of Patent: Aug. 26, 2014

(54) YELLOW PEA SEED PROTEIN-DERIVED PEPTIDES

(75) Inventors: Rotimi Aluko, Winnipeg (CA); Jianping Wu, Edmonton (CA); Harold Aukema, Winnipeg (CA)

(73) Assignee: University of Manitoba, Manitoba (CA)

(*) Notice: Subject to any disclaimer, the term of this patent is extended or adjusted under 35 U.S.C. 154(b) by 0 days.

(21) Appl. No.: 13/504,512

(22) PCT Filed: Oct. 28, 2010

(86) PCT No.: PCT/CA2010/001710
§ 371 (c)(1),
(2), (4) Date: Aug. 21, 2012

(87) PCT Pub. No.: WO2011/050471
PCT Pub. Date: May 5, 2011

(65) Prior Publication Data
US 2012/0329716 A1  Dec. 27, 2012

Related U.S. Application Data

(60) Provisional application No. 61/255,523, filed on Oct. 28, 2009.

(51) Int. Cl.
*A61K 38/08* (2006.01)
*C07K 7/06* (2006.01)
*A61P 13/12* (2006.01)
*C07K 14/415* (2006.01)

(52) U.S. Cl.
CPC . *A61K 38/08* (2013.01); *C07K 7/06* (2013.01); *C07K 14/415* (2013.01)
USPC .......................... 514/15.4; 530/329; 514/21.8

(58) Field of Classification Search
CPC ......... A61K 38/00; A61K 38/08; C07K 7/00; C07K 14/415; C07K 7/06; A23L 1/3053; A23V 2002/00; A23V 2250/54246; A23V 2200/3202; A23V 2250/70; A23V 2250/156; A23V 2250/628; A23V 2250/548
See application file for complete search history.

(56) References Cited

U.S. PATENT DOCUMENTS

| | | | |
|---|---|---|---|
| 5,789,384 | A | 8/1998 | Khavinson et al. |
| 5,824,315 | A | 10/1998 | Nag |
| 6,184,204 | B1 | 2/2001 | Boots et al. |
| 6,380,183 | B1 * | 4/2002 | Schreiner et al. ........ 514/211.06 |
| 2004/0031072 | A1 | 2/2004 | La Rosa et al. |
| 2006/0123505 | A1 | 6/2006 | Kikuchi et al. |
| 2007/0032413 | A1 | 2/2007 | Rosen |
| 2007/0203060 | A1 | 8/2007 | Sidelman |
| 2009/0130103 | A1 | 5/2009 | Nellis et al. |
| 2009/0137046 | A1 | 5/2009 | Calixto et al. |

FOREIGN PATENT DOCUMENTS

| | | |
|---|---|---|
| EP | 2100901 A1 | 9/2009 |
| EP | 2161028 A1 | 3/2010 |
| WO | WO 94/12640 | 6/1994 |
| WO | WO 01/32677 A1 | 11/1999 |
| WO | WO 02/094981 A2 | 11/2002 |
| WO | WO 2004/091548 A2 | 10/2004 |
| WO | WO 2007/027559 A2 | 3/2007 |
| WO | WO 2007/043900 A1 | 4/2007 |
| WO | WO 2007/074456 A2 | 7/2007 |
| WO | WO 2008/008766 A2 | 1/2008 |

OTHER PUBLICATIONS

Vermeirssen et al, A quantitative in silico analysis calculates the angiotensin I converting enzyme (ACE) inhibitory activity in pea and whey protein digests, Biochimie, 2004, 86, pp. 231-239.*
Ecder et al, Diuretics versus Angiotensin-Converting Enzyme Inhibitors in Autosomal Dominant Polycystic Kidney Disease, Am. J. Nephrol, 2001, 21, pp. 98-103.*
Wu, J. et al. 2006, "Structural Requirements of Angiotensin I-Converting Enzyme Inhibitory Peptides . . . " J. Agric. Food Chem., vol. 54, pp. 732-738.
Li, H. and Aluko, R.E., Epublished, Oct. 7, 2010, "Identification and Inhibitory Properties of Multifuncation . . . " Agric. Food Chem., vol. 58, pp. 11471-11476.
Szelke, M. et al., 1982, "Potent New Inhibitors of Human Renin", Nature vol. 299, pp. 555-557, ISSN: 0028-0836.
Zaman et al., 2002 "Drugs Targeting the Renin-Angiotensin-Aldosterone System", Nature Reviews, vol. 1, pp. 621-636.
Wang et al. 1993, "A Continuous Flourescence Assay of Renin Activity", Analytical Biochemistry, vol. 210, pp. 351-259.
Waeber et al., 1995 Ch. 172 "Angiotensin-Converting Enzyme Inhibitors in Hypertension", Hypertension: Pathophsiology, Diagnosis and Management, Second Edition. Raven Press Ltd.
Verma & Strauss, 2004, "Angiotensin Receptor Blockers and Myocardial Infarction", BMJ, vol. 329, pp. 1248-1249.
Hatae et al., 1992, "Kinetic Studies on Recombinant Human Renin . . . ", Biomedical Research, vol. 13, pp. 381-383.
Slater et al. 1988, "Clinical Profile of Angioedema Associated with Angiotensin Converting-Enzyme Inhibition", JAMA, vol. 260, No. 7, pp. 967-970.
Slater & Strout 1981, "Pure Human Renin", The Journal of Biological Chemistry, vol. 256, No. 15, pp. 8164-8171.

(Continued)

*Primary Examiner* — Julie Ha
*Assistant Examiner* — Li Ni Komatsu
(74) *Attorney, Agent, or Firm* — Lorelei G. Graham

(57) ABSTRACT

The instant invention relates to peptides obtained from the enzymatic hydrolysis of yellow pea seed proteins that are capable of lowering the blood pressure and reducing the effects of kidney disease in a subject by inhibiting or reducing the affinity of the enzymes in the renin-angiotensin system for their substrates, specifically renin, to compositions comprising said peptides and to uses thereof.

10 Claims, 16 Drawing Sheets

(56) References Cited

OTHER PUBLICATIONS

Skeggs et al. 1955, "The Preparation and Function of the Hypertensin-Converting Enzyme", Dept. of Medicine and Surgery, Veterans Admin Hospital, Western Reserve University, CL.

Roberts et al. 1999, "Effect of Chain Length on Absorption of Biologically Active Peptides . . . " Digestion, vol. 60, pp. 332-337.

Poulsen et al. 1976, "On the Specificity of Human Renin Studies with Peptide Inhibitors" Biochimica et Biophysica Acta., vol. 452, pp. 533-537.

Parikh & Cuatrecasas 1973, "Substrate Analog Competitive Inhibitors of Human Renin", Biochemical & Biophysical Research Comm., vol. 54, No. 4, pp. 1356-1361.

Oparil & Haber, "Medical Progress", The New England Journal of Medicine, vol. 291, No. 8, pp. 389-401, 1974.

Loboda et al., 2000, "A Tandem Quadrupole/Time-of-Flight mass Spectrometer . . . ", Rapid Communications, vol. 14, pp. 1047-1057.

Holzman et al., 1991, "Characterization of Recombinant Human Renin . . . " Journal of Protein Chemistry, vol. 10. No. 5, pp. 553-563.

Wong et al., 2009, "Blood Pressure Lowering Efficacy of Angiotensin . . . ", The Cochrane Collaboration, published by John Wiley & Sons Ltd.

Haber, Edgar 1986, "Renin Inhibitors", Hypertension Editorial, vol. 8, No. 12, pp. 1093-1094.

Guo et al. 2005, "Effect of the Phosphate Group with Different Negative Charges . . . " Int. Journal of Peptide Research, vol. 11, No. 2, pp. 159-165.

Sanchez et al. 2007, "Double Acylation for Identification of Amino-Terminal Peptides . . . " Rapid Communications, vol. 21, pp. 2237-2244.

Cutler et al. 2008, "Trends in Hypertension Prevalence, Awareness, Treatment . . . " Journal of American Heart Assoc., vol. 52; pp. 818-827.

Cushman & Ondetti 1999, Design of Angiotensin Converting Enzyme Inhibitors, Nature Medicine, vol. 5, No. 10, pp. 1110-1112.

Acharya et al. 2003, "Ace Revisitied: A New Target for Structure-Based Drug Design", Nature Reviews, vol. 2, pp. 891-902.

Abdi et al. 2002, "Angiotensin II Receptor Blocker-Associated Angioedema . . . ", Pharmacotherapy, vol. 22, No. 9, pp. 1173-1175.

Haber, Edgar, 1989, "Why Renin Inhibitors", Journal of Hypertension, vol. 7, (Suppl 2); S81-S86.

Cumin et al. 1987, "A Potent Radiolabled Human Renin Inhibitor . . . " Biochemistry, vol. 26, pp. 7615-7621.

Gregg B Fields & Richard L. Noble, 1990 "Solid Phase Peptide Synthesis . . . " Int. J. Peptide Protein Res., vol. 35, pp. 161-214.

Kamper et al., 2009, "Hypertension Og Nyresygdom", Hypertension and Renal Disease, vol. 171, Issue 25, pp. 2109-2113.

Merrifield, R.B. 1963 "Solid Phase Peptide Synthesis" J. Amer. Chem Soc. vol. 85, pp. 2149-2154.

Foltmann & Pedersen 1977, Institute of Biochemical Genetics, Uniersity of Copenhagen, Garimagsgade 2A, DK-1353 Copenhagen pp. 3-22.

\* cited by examiner

SEQUENCE LISTING

<160> NUMBER OF SEQ ID NOS: 28

<210> SEQ ID NO 1
<211> LENGTH: 2
<212> TYPE: PRT
<213> ORGANISM: Pisum sativum

<400> SEQUENCE: 1

Ile Arg
1

<210> SEQ ID NO 2
<211> LENGTH: 2
<212> TYPE: PRT
<213> ORGANISM: Pisum sativum

<400> SEQUENCE: 2

Lys Phe
1

<210> SEQ ID NO 3
<211> LENGTH: 2
<212> TYPE: PRT
<213> ORGANISM: Pisum sativum

<400> SEQUENCE: 3

Glu Phe
1

<210> SEQ ID NO 4
<211> LENGTH: 2
<212> TYPE: PRT
<213> ORGANISM: Pisum sativum

<400> SEQUENCE: 4

Leu Arg
1

<210> SEQ ID NO 5
<211> LENGTH: 2
<212> TYPE: PRT
<213> ORGANISM: Pisum sativum

<400> SEQUENCE: 5

Asn Arg
1

<210> SEQ ID NO 6
<211> LENGTH: 2
<212> TYPE: PRT
<213> ORGANISM: Pisum sativum

<400> SEQUENCE: 6

Gln Phe
1

<210> SEQ ID NO 7
<211> LENGTH: 2
<212> TYPE: PRT
<213> ORGANISM: Pisum sativum

<400> SEQUENCE: 7

Ser Phe
1

<210> SEQ ID NO 8
<211> LENGTH: 2
<212> TYPE: PRT
<213> ORGANISM: Pisum sativum

<400> SEQUENCE: 8

Tyr Arg
1

<210> SEQ ID NO 9
<211> LENGTH: 2
<212> TYPE: PRT
<213> ORGANISM: Pisum sativum

<400> SEQUENCE: 9

Phe Thr
1

<210> SEQ ID NO 10
<211> LENGTH: 2
<212> TYPE: PRT
<213> ORGANISM: Pisum sativum

<400> SEQUENCE: 10

Arg Phe
1

<210> SEQ ID NO 11
<211> LENGTH: 2
<212> TYPE: PRT
<213> ORGANISM: Pisum sativum

<400> SEQUENCE: 11

Phe Lys
1

<210> SEQ ID NO 12
<211> LENGTH: 2
<212> TYPE: PRT
<213> ORGANISM: Pisum sativum

<400> SEQUENCE: 12

Phe Gln
1

<210> SEQ ID NO 13
<211> LENGTH: 3
<212> TYPE: PRT
<213> ORGANISM: Pisum sativum

<400> SEQUENCE: 13

Trp Leu Pro
1

```
<210> SEQ ID NO 14
<211> LENGTH: 4
<212> TYPE: PRT
<213> ORGANISM: Pisum sativum

<400> SEQUENCE: 14

Arg Ala Ala Pro
1

<210> SEQ ID NO 15
<211> LENGTH: 3
<212> TYPE: PRT
<213> ORGANISM: Pisum sativum

<400> SEQUENCE: 15

Trp Met Pro
1

<210> SEQ ID NO 16
<211> LENGTH: 5
<212> TYPE: PRT
<213> ORGANISM: Pisum sativum

<400> SEQUENCE: 16

His Pro Gly Ala Gly
1               5

<210> SEQ ID NO 17
<211> LENGTH: 4
<212> TYPE: PRT
<213> ORGANISM: Pisum sativum

<400> SEQUENCE: 17

Arg Ser Pro Asp
1

<210> SEQ ID NO 18
<211> LENGTH: 4
<212> TYPE: PRT
<213> ORGANISM: Pisum sativum

<400> SEQUENCE: 18

Trp Pro His Thr
1

<210> SEQ ID NO 19
<211> LENGTH: 4
<212> TYPE: PRT
<213> ORGANISM: Pisum sativum

<400> SEQUENCE: 19

Tyr Pro Arg Glu
1

<210> SEQ ID NO 20
<211> LENGTH: 7
<212> TYPE: PRT
<213> ORGANISM: Pisum sativum

<400> SEQUENCE: 20

Ser Asn Ile Leu Glu Ala Ala
1               5

<210> SEQ ID NO 21
<211> LENGTH: 7
```

```
<212> TYPE: PRT
<213> ORGANISM: Pisum sativum

<400> SEQUENCE: 21

Tyr Ala Gly Val Ser Leu Ile
1               5

<210> SEQ ID NO 22
<211> LENGTH: 7
<212> TYPE: PRT
<213> ORGANISM: Pisum sativum

<400> SEQUENCE: 22

Ala His Pro Val Ala Ile Asn
1               5

<210> SEQ ID NO 23
<211> LENGTH: 6
<212> TYPE: PRT
<213> ORGANISM: Pisum sativum

<400> SEQUENCE: 23

Ala Asp Met Phe Pro Phe
1               5

<210> SEQ ID NO 24
<211> LENGTH: 6
<212> TYPE: PRT
<213> ORGANISM: Pisum sativum

<400> SEQUENCE: 24

Thr Asn Pro Phe Pro Phe
1               5

<210> SEQ ID NO 25
<211> LENGTH: 8
<212> TYPE: PRT
<213> ORGANISM: Pisum sativum

<400> SEQUENCE: 25

Asn Phe Leu Ala Gly Pro Ser Asp
1               5

<210> SEQ ID NO 26
<211> LENGTH: 12
<212> TYPE: PRT
<213> ORGANISM: Pisum sativum

<400> SEQUENCE: 26

Tyr Lys Lys Ser Val Ser Ser Glu Ser Asp Pro Phe
1               5                   10

<210> SEQ ID NO 27
<211> LENGTH: 2
<212> TYPE: PRT
<213> ORGANISM: Pisum sativum

<400> SEQUENCE: 27

Ile Trp
1

<210> SEQ ID NO 28
<211> LENGTH: 2
<212> TYPE: PRT
<213> ORGANISM: Pisum sativum
```

```
<400> SEQUENCE: 28

Leu Trp
1
```

YELLOW PEA SEED PROTEIN-DERIVED PEPTIDES

CROSS-REFERENCE TO RELATED APPLICATIONS

This application claims the benefit of US Provisional patent application No. 61/255523 filed Oct. 28, 2009 and Internatonal patent application no. PCT/CA2010/001710 filed Oct. 28, 2010.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to novel peptides that are capable of reducing blood pressure in a subject. More specifically, the present invention relates to novel peptides obtained from enzymatic hydrolysis of yellow pea seed proteins capable of lowering the blood pressure and reducing the effects of kidney disease in a subject by inhibiting or reducing the affinity of the enzymes in the renin-angiotensin system for their substrates, specifically renin.

2. Description of Related Art

Hypertension is a chronic disease which afflicts about 21% of the population of the United States (Cutler et al., 2008). Chronic hypertension can lead to Cardiovascular Disease (CVD) and Chronic Kidney Disease (CKD) which can be detected in 10% of the population (Kamper et al., 2009).

The renin-angiotensin system (RAS) plays a central role in the regulation of blood pressure and electrolyte metabolism (Oparil & Haber, 1974; Zaman, Oparil, & Calhoun, 2002). Renin is the first and rate-determining enzyme in RAS, catalyzing the hydrolytic release of Angiotensin I (Ang I) from the N-terminal end of angiotensinogen. Angiotensin 1 is subsequently converted into a potent pressor octapeptide, angiotensin II, by the angiotensin I-converting enzyme (ACE). ACE is one of the most extensively studied enzymes and its predominant physiological function in cardiovascular homeostasis is well documented (see for example Skeggs, Kahn, & Shumway, 1956). Blockade of Angiotensin II accumulation through the inhibition of ACE has been proven as a validated treatment approach for hypertension (Cushman & Ondetti, 1999). However, the long-term treatment by ACE inhibitors (ACEI) seems not to completely suppress the circulating renin-angiotensin system as plasma Angiotensin II (Ang II) and aldosterone levels tend to return toward pre-treatment values. The presence of non-RAS enzymes, including tonin and cathepsin, are capable to generate Ang II directly from angiotensinogen that contribute to the elevated Angiotensin II and aldosterone levels after ACEI treatment [Zaman, Oparil, & Calhoun, 2002]. ACE is an enzyme with broad substrates and inhibitors specificities (Acharya, Sturrock, Riordan, & Ehlers, 2003). In addition of the inhibition of conversion of Ang I into Ang II, ACEI also inhibits the degradation of bradykinin, which may be related to its side effects observed with ACE-inhibitory drugs such as the rare cases of angioneurotic edema and the more frequent occurrence of cough (Acharya, Sturrock, Riordan. & Ehlers, 2003; Slater et al 1988; Waeber, Nussberger, & Brunner, 1995).

Administering subjects with Angiotensin II Receptor Blockers (ARBs), which inhibit binding of Angiotensin II to the AT1 receptors, is a common alternative to use of ACE inhibitors to treat hypertension (Heran B S, Wong M M Y, Heran I K, & Wright J M, 2008). While ARBs are not responsible for degradation of bradykinin, they can still lead to angioedema (Abdi R, Dong VM, Lee CJ, & Ntoso KA, 2002). Further side effects associated with use of ARBs are a higher risk of myocardiac infarction (Varma S & Strauss M., 2004).

In contrast to ACE, renin is a highly specific enzyme, having angiotensinogen as its only known physiological substrate (Foltmann & Pedersen, 1977). Inhibiting renin at this step would be expected to block the classic RAS cascade, and therefore would have blood pressure lowering effect and avoid ACEI-related side effects (Haber, 1989). Although very attractive, unfortunately, research on renin inhibitors have been proven unsuccessful for clinical application due mainly to the lack of oral bioavailability or efficacy (Poulsen, Burton, & Haber, 1976; Haber 1986).

In view of the current state of the art, it would be advantageous to provide a compound and a method that: can effectively reduce high blood pressure, can be obtained from natural sources, can be delivered orally, can be capable of inhibiting renin and can be easy to manufacture, and that can overcome the current limitations to high blood pressure treatments, including common side effects and decreased efficacy over long term treatment.

BRIEF SUMMARY OF THE INVENTION

The current invention relates to the discovery of novel peptides.

Thus, in one aspect. the present invention provides for an isolated peptide comprising an amino acid sequence of SEQ ID NO. 1 to SEQ ID NO. 28.

In another aspect, the present invention provides for an isolated DNA, said DNA comprising a nucleotide sequence encoding for an isolated peptide comprising an amino acid sequence of SEQ. ID No. 1 to SEQ ID NO. 28.

The present invention also relates to the discovery of novel peptides capable of reducing high blood pressure in a subject.

In another aspect, the present invention provides for a composition comprising one or more peptides comprising an amino acid sequence of SEQ ID NO. 1 to SEQ ID NO. 28.

Thus, according to yet another aspect, the present invention provides for a peptide capable of reducing blood pressure in a subject, characterized in that said peptide comprises at least one of the amino acid sequences of SEQ ID NO. 1 to SEQ ID NO. 28.

In another aspect, the present invention provides for a peptide capable of inhibiting or reducing the production of angiotensin I or angiotensin II in a subject, characterized in that said peptide comprises at least one of the amino acid sequences of SEQ ID NO. 1 to SEQ ID NO. 28.

In another aspect, the present invention provides for a peptide capable of inhibiting or reducing the production of angiotensin I in a subject, characterized in that said peptide comprises at least one of the amino acid sequences of SEQ ID NO. 1 to SEQ ID NO. 28.

In another aspect, the present invention provides for a peptide capable of inhibiting or reducing the affinity of renin for a substrate, characterized in that said peptide comprises at least one of the amino acid sequences of SEQ ID NO. 1 to SEQ ID NO. 28.

In another aspect, the present invention provides for a peptide capable of inhibiting or reducing the affinity of ACE for angiotensin I, characterized in that said peptide comprises at least one of the amino acid sequences of SEQ ID NO. 1 to SEQ ID NO. 28.

In another aspect, the present invention provides for compositions that are useful in the prevention and/or treatment of conditions or diseases associated with high blood pressure or other disturbances of cardiac function, including hypertension, cardiovascular disease and chronic kidney disease, characterized in that said compositions comprise one or more peptides listed in SEQ ID NO. 1 to SEQ ID NO. 28.

In another aspect, the present invention provides for methods of treating a condition or a disease associated with high blood pressure or disturbances of cardiac function in a subject, characterized in that said method comprises administering to the subject a composition comprising one or more peptides listed in SEQ ID NO. 1 to SEQ ID NO. 28.

In another aspect, the present invention provides for a composition comprising one or more peptides comprising an amino acid sequence of SEQ ID NO. 1 to SEQ ID NO. 28 capable of reducing blood pressure in a subject.

In another aspect, the present invention provides for a composition comprising one or more peptides comprising an amino acid sequence of SEQ ID NO. 1 to SEQ ID NO. 28 capable of reducing the effects of kidney disease in a subject.

Advantages of the present invention include:
(a) small peptides are obtained from a natural source (yellow pea seeds);
(b) the small peptides are effective in reducing high blood pressure and other related conditions;
(c) given their small size, the peptides of the invention are easily absorbed by the digestive tract and can therefore be delivered orally;
(d) given that they inhibit renin, the rate limiting enzyme in the RAS pathway, the small peptides of the present invention can overcome the current limitations to high blood pressure treatments, including common side effects and decreased efficacy over long term treatment.

BRIEF DESCRIPTION OF THE DRAWINGS

The invention will be better understood and objects of the invention will become apparent when consideration is given to the following detailed description thereof. Such description makes reference to the annexed drawings wherein:

FIG. 8 illustrates the effect of yellow pea seed protein hydrolysate on systolic blood pressure of PKD rats.

Figure 1:
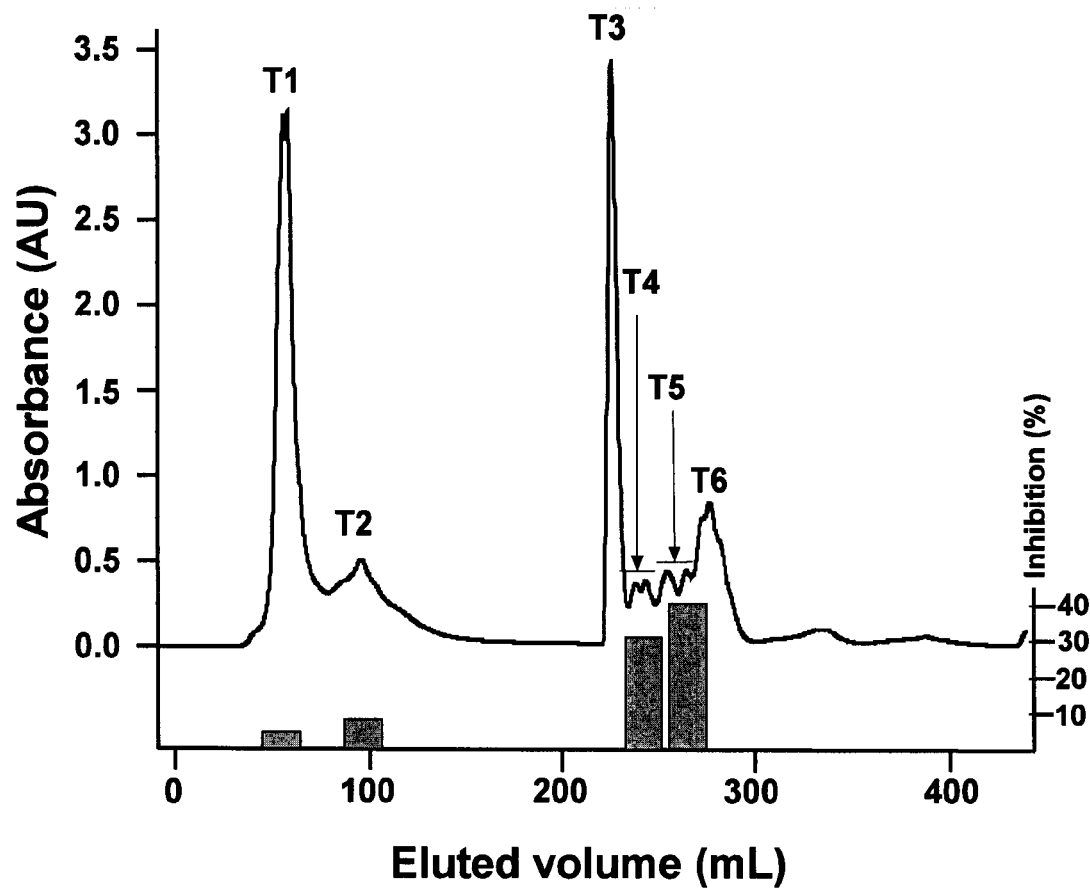
FIG. 1 illustrates the renin inhibiting activity of the active fractions (T4 and T5) of yellow pea protein hydrolysate. The active fractions were shown to inhibit the activity of purified human recombinant renin from Cayman Chemical (Ann Arbor, Mich., USA) following the manufacturers protocol.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE INVENTION

The invention will be explained in details by referring to the figures.

In one aspect, the present invention provides for an isolated peptide comprising a sequence of SEQ ID NO. 1 to SEQ ID NO. 28.

In another aspect, the present invention provides for a peptide, said peptide comprising amino acid sequences of SEQ ID NO. 1 to SEQ ID NO. 28, wherein said peptide is capable of reducing blood pressure in a subject.

Figure 8:
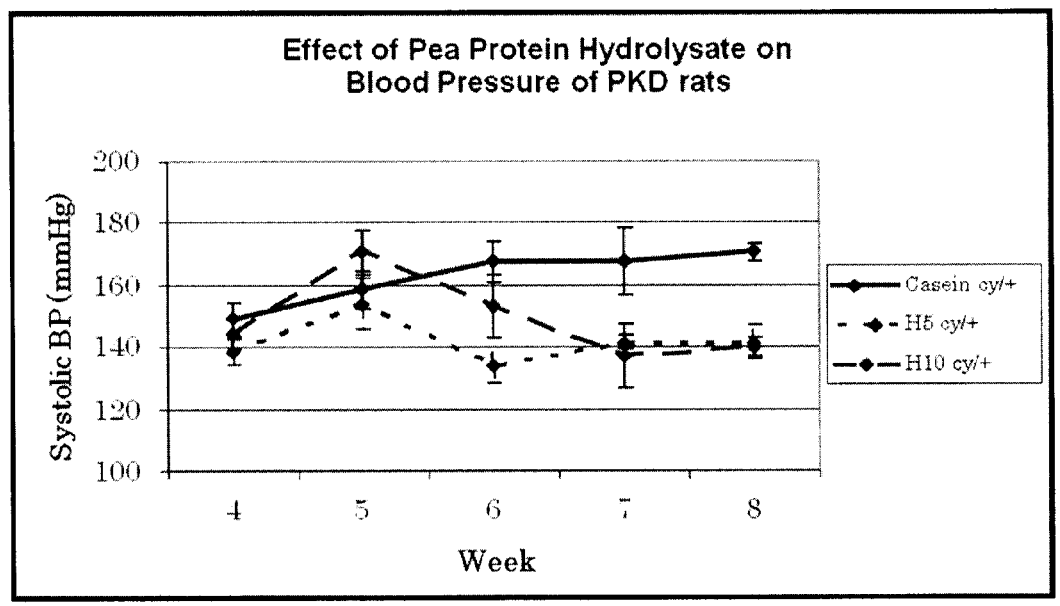
FIG. 8 illustrates the effect of yellow pea seed protein hydroiysate on systolic blood pressure of PKD rats.

The Applicant has identified a set of peptides obtained from yellow pea protein hydrolysates that are capable of reducing blood pressure in a subject. As illustrated in FIG. 8, using a rat model for polycystic kidney disease (PKD), the Applicant discovered that selected peptide fractions obtained from yellow peas are capable of reducing blood pressure in a subject.

Figure 5:
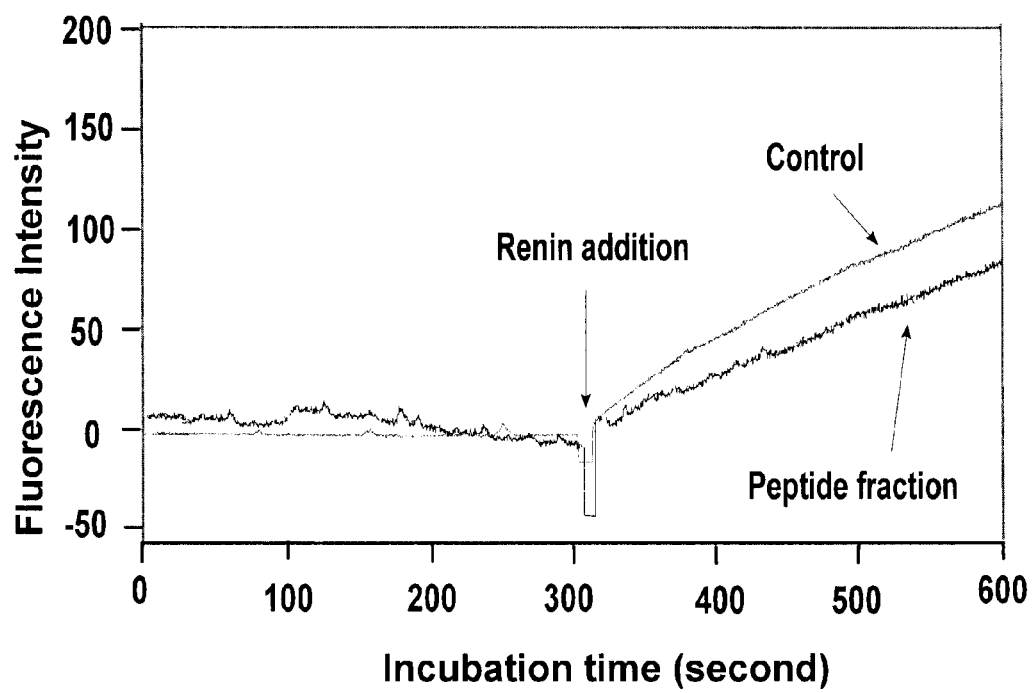
FIG. 5 illustrates the typical in vitro fluorometric assay demonstrating inhibition of human recombinant renin activity by T4 or T5 peptide fractions
Figure 9:
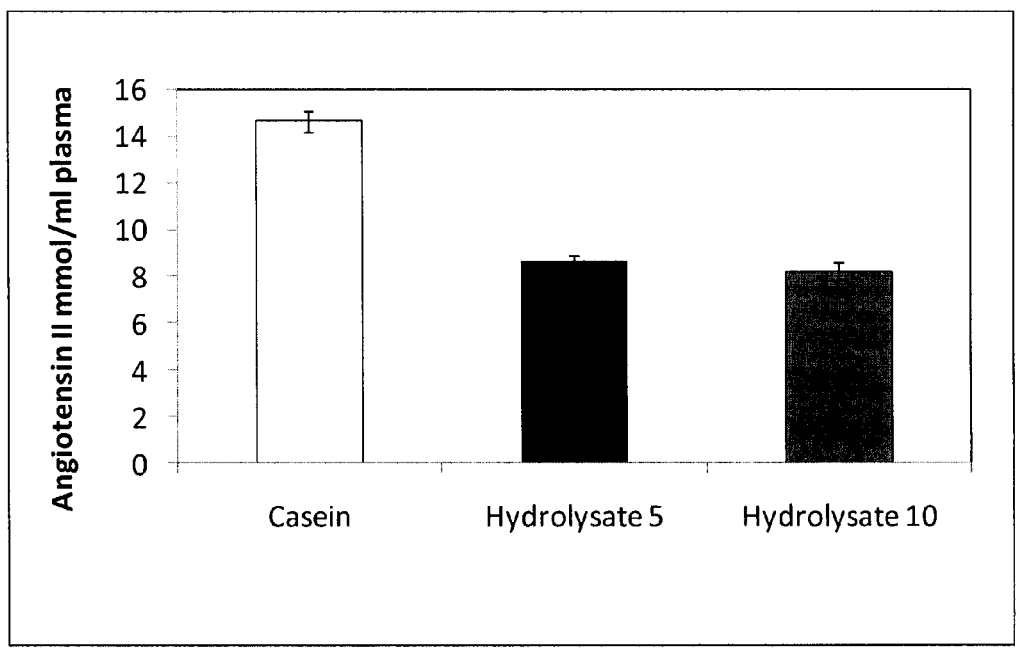
FIG. 9 illustrates the effect of diet containing yellow pea seed protein hydrolysate on angiotensin II levels in plasma of PKD rats.
Figure 10:
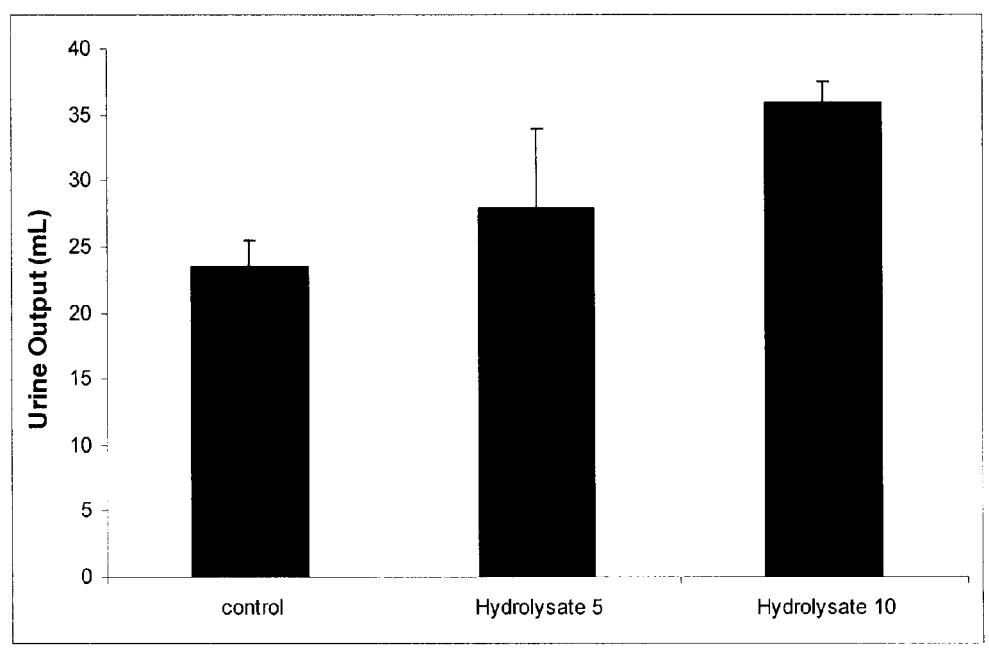
FIG. 10 illustrates the effect of diet containing yellow pea seed protein hydrolysate on urine production in PKD rats.
Figure 11:
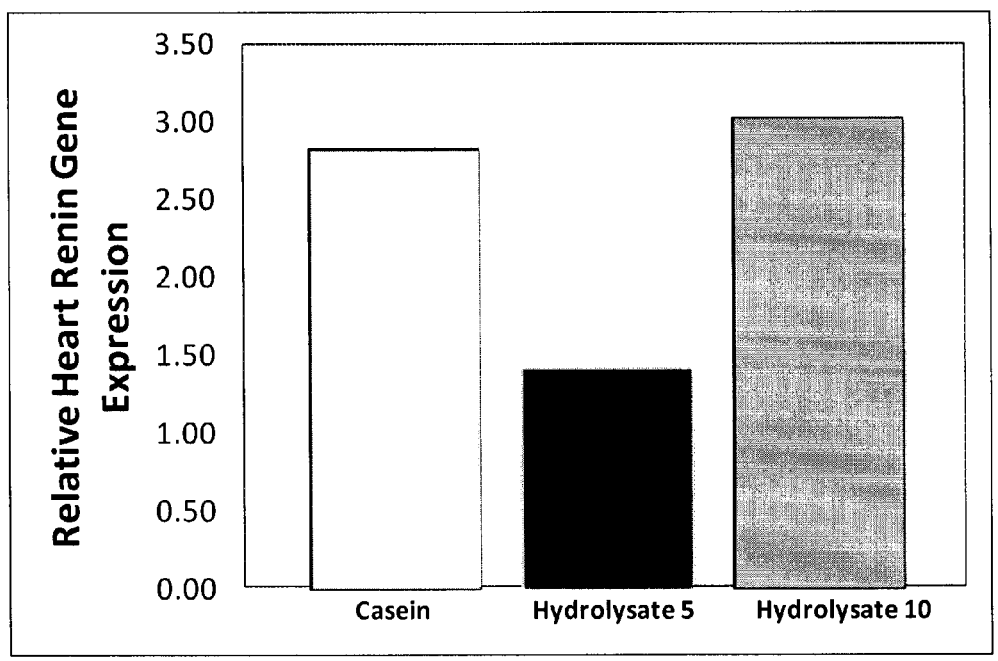
FIG. 11 illustrates the effect of diet containing yellow pea seed protein hydrolysate on heart renin gene expression in PKD rats.

FIG. 9 illustrates that yellow pea protein hydrolysates are capable reducing the levels of angiotensin II (Ang II) in plasma of PKD rats. FIGS. 10 and 11 illustrate that the yellow pea protein hydrolysates of the invention may exert its blood pressure lowering effect by reducing the level of renin gene expression. FIG. 5 illustrates that the yellow pea protein hydrolysate of the invention comprising peptides of SEQ ID NO. 1 to SEQ ID NO. 28 also directly inhibit human recombinant renin activity.

As provided in the Examples, the Applicant identified the peptides in bioactive fractions, which are listed in the Sequencing Listing as SEQ ID NOs. 1 to 28 (FIGS. 1-4). Table 1 illustrates that the peptides SEQ ID NO. 1 to SEQ ID NO. 28 identified within the bioactive fractions of yellow pea protein hydrolysate also directly inhibit human recombinant renin activity.

Figure 16:
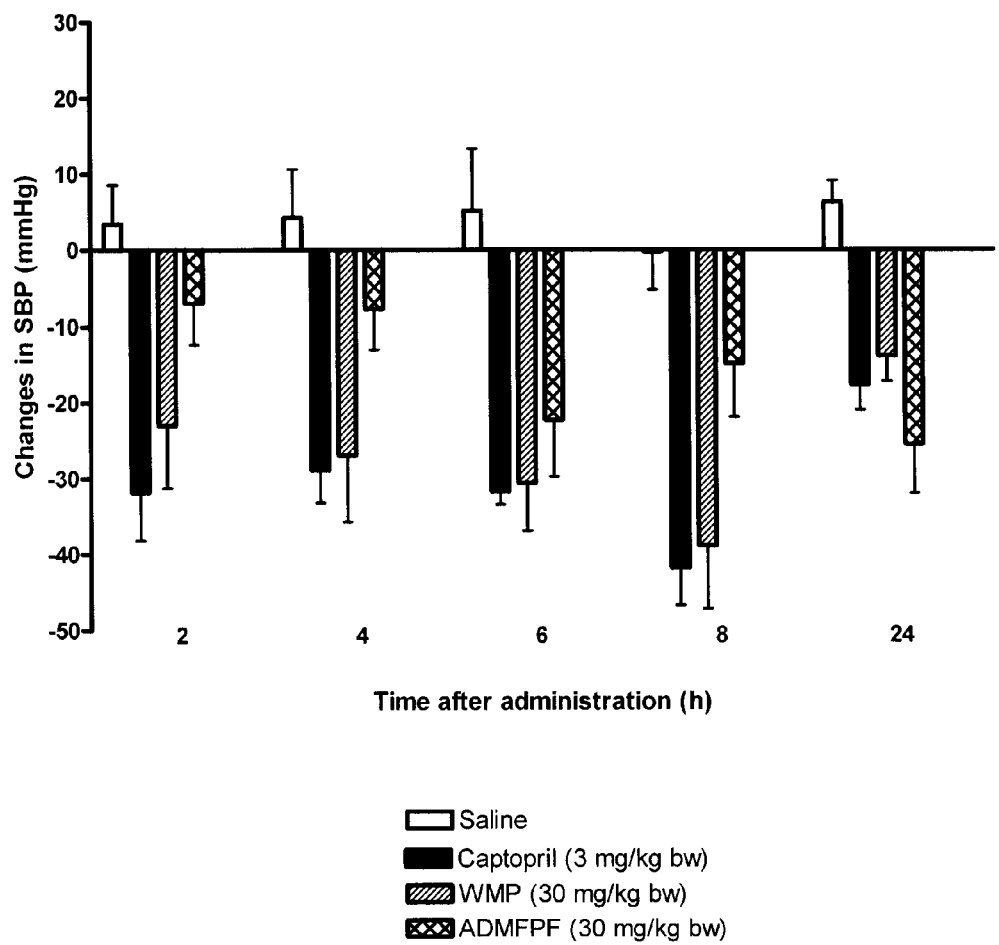
FIG. 16 illustrates the effect of diet containing WMP (SEQ ID NO. 15) and ADMFPF (SEQ ID NO. 23) on blood pressure of spontaneously hypertensive rats over a time-course.

As illustrated in FIG. 16 the Applicant performed a proof of principle test with 2 peptides identified in the bioactive fractions, SEQ ID NO. 15 and SEQ ID NO. 23, using a Spontaneously Hypertensive Rat model. In the instant invention, it is determined that the peptides obtained from the bioactive fractions of yellow pea protein hydrolysate are capable of reducing blood pressure in a subject. The test conducted on the identified 2 peptides noted above is applicable to the remaining 26 peptides showing renin inhibiting activity identified herein.

Figure 15:
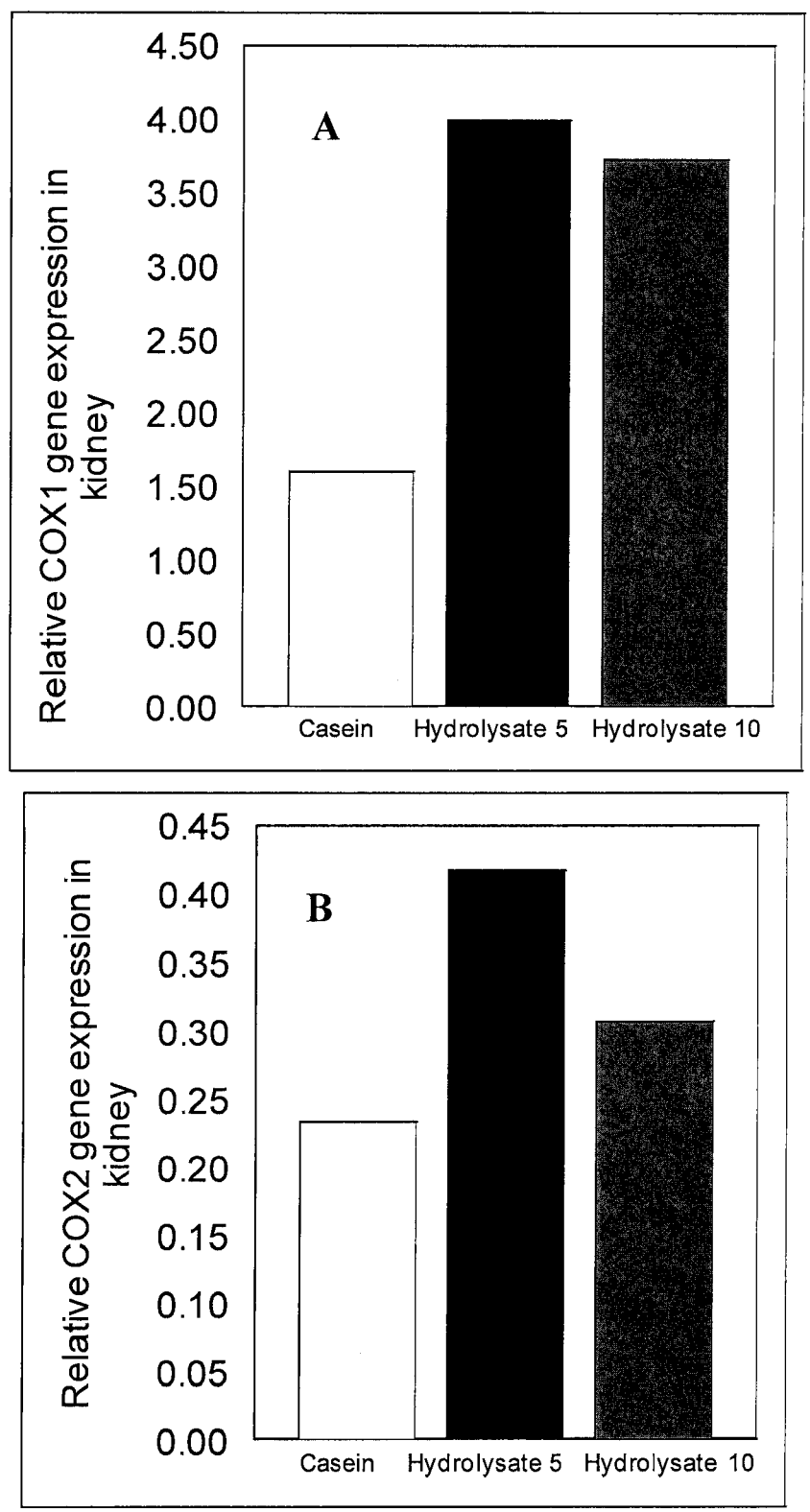
FIG. 15 illustrates the effect of diet containing yellow pea seed protein hydrolysate on kidney COX-1 (A) and COX-2 (B) gene expressions in PKD rats.

The Applicant shows in FIG. 15 that Cyclooxygenase-1 (COX-1) and cyclooxygenase-2 (COX-2) mRNA levels were significantly increased in PKD rats by a diet of pea protein hydrolysate. COX-1 and COX-2 are believed to produce eicosanoids that enhance blood flow during kidney disease. Therefore, the higher levels of COX-1 and COX-2 associated with consumption of the pea protein hydrolysate could be related with the observed increases in urine production (FIG. 10) as a result of better blood flow within the kidney tissues. These results indicate that the consumption of pea protein hydrolysate by a subject can lead to a reduction of the effects of kidney disease in a subject.

Thus, in the instant invention, it is determined that the yellow pea protein hydrolysate comprising of peptides comprising a sequence of SEQ ID NO. 1 TO SEQ ID NO. 28 capable of reducing the effects of kidney disease in a subject.

Taken together, the present invention demonstrates a set of peptides that in aspects are derived from yellow pea proteins and in other aspects based on artificial peptide sequences. The term "peptide" as used herein is defined as a chain of amino acid residues, usually having a defined sequence. As used herein the term peptide is mutually inclusive of the terms "peptides" and "proteins".

The peptides of the present invention may be modified by the addition cysteine residues to one or both ends of the peptides to circularize the peptides by the formation of disulfide bond formation. The peptides of the present invention may be modified by the addition of phosphorus and acetyls groups. Phosphorylation is one of the most common protein modifications that occur in animal cells [Guo, Yan-Ting et al. International Journal of Peptide Research and Therapeutics 11:159 (2005)]. It occurs most commonly on threonine, serine and tyrosine residues and plays critical roles in the regulation of many cellular processes including: cell cycle, growth, apoptosis and differentiation [Guo, Yan-Ting et al. International Journal of Peptide Research and Therapeutics 11:159 (2005)]. This procedure is possible because some of the peptides of the present invention contain tyrosine and because an acyl group can be added to N-terminal amino acid [Aniel A. et al. Rapid Comm Mass Spectr. 21:2237 (2007)]. The two amino acids tryptophan and tyrosine in the peptides of the invention may be substituted with other amino acids to evaluate their effects on peptide activities.

The peptides of the invention are small peptides, that is they may be of about at least 2 amino acids in length to about 12 amino acids in length and include any ranges of length therein (i.e. 2, 3, 4, 5, 6, 7, 8, 9, 10, 11 or 12) as is understood by one of skill in the art. Peptides of over about 12 amino acids in length are also encompassed by the present invention. The length of peptide being only restricted by its ability to reduce blood pressure in a subject or its ability to reduce the effects of kidney disease in a subject. The peptides of the invention may also include dimers and trimers of the peptides as well as additional stabilizing flanking sequences as is understood by those of skill in the art and described for example in U.S. Pat. Nos. 5,824,315 and 6,184,204 (the disclosures of which are incorporated herein by reference in their entirety).

A multimer according to the invention can either be a homomer, consisting of a multitude of the same peptide, or a heteromer consisting of different peptides. As stated, the amino acid sequences of the peptides according to the invention can be flanked by random amino acid sequences. Preferred are flanking sequences that have a stabilizing effect on the peptides, thus increasing their biological availability. In addition, other peptidomimetics are also useful in the peptides of the present invention. The peptides of the invention also encompass peptides that have been modified by, for example, phosphorylation, glycosylation or lipidation. Furthermore, the peptides of the present invention may also encompass "functionally equivalent variants" or "analogues" of the peptides. As such, this would include but not be limited to peptides and polypeptides with partial sequence homology, peptides having one or more specific conservative and/or non-conservative amino acid changes and peptide conjugates which do not alter the biological or structural properties of the peptide (i.e. the ability to induce an antioxidative response).

In terms of "functional analogues", it is well understood by those skilled in the art, that inherent in the definition of a biologically functional peptide analogue is the concept that there is a limit to the number of changes that may be made within a defined portion of the molecule and still result in a molecule with an acceptable level of equivalent biological activity, which, in this case, would include the ability to induce an antioxidative reaction. A plurality of distinct peptides/proteins with different substitutions may easily be made and used in accordance with the invention. it is also understood that certain residues are particularly important to the biological or structural properties of a protein or peptide such as residues in the receptor recognition region, such residues of which may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc.

Examples of conservative substitutions include the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the peptide.

Examples of such conservative changes are well-known to the skilled artisan and are within the scope of the present invention. Conservative substitution also includes the use of a chemically derivatized residue in place of a non-derivatized residue provided that the resulting peptide is a biologically functional equivalent to the peptides of the invention. Therefore, the peptides of the present invention encompass a peptide having an amino acid sequence that differs from SEQ ID Nos. 1-28. The peptides of the invention also encompass a peptide having an amino acid sequence that differs from SEQ ID Nos. 1-28 by a single mutation, where the single mutation represents a single amino acid deletion, insertion or substitution.

The novel peptides of the invention may be further isolated and purified from yellow pea by methods selected on the basis of properties revealed by its sequence. Purification can be achieved by protein purification procedures such as chromatography methods (gel filtration, ion-exchange and immunoaffinity), by high-performance liquid chromatography (HPLC, RP-HPLC, ion-exchange HPLC, size-exclusion HPLC, high-performance chromatofocusing and hydrophobic interaction chomatography) or by precipitation (immunoprecipitation). Polyacrylamide gel electrophoresis can also be used to isolate the proteins based on the molecular weight of the protein, charge properties and hydrophobicity. The purified proteins can be used in further biochemical analyses to establish secondary and tertiary structure which may aid in the design of pharmaceuticals to interact with the protein, alter the protein charge configuration or charge interaction with other proteins or alter its function.

The novel peptides of the present invention may be artificially made by methods known to those of skill in the art most notably and preferably by chemical synthesis using techniques well known in the chemistry of proteins such as solid phase synthesis [J. Am. Chem. Assoc. 65:2149 (1964); J. Amer. Chem. Soc. 85:2149 (1963); and Int. J. Peptide Protein Res. 35:161-214 (1990)] or synthesis in homogenous solution [Methods of Organic Chemistry, E. Wansch (Ed.) Vol. 15, pts. I and I 1, Thieme, Stuttgart (1987)] to generate synthetic peptides.

Alternatively, the peptides of the invention may be made by the use of recombinant DNA techniques known to one skilled in the art.

It is further contemplated that the invention encompasses vectors which comprise nucleic acids coding for at least one of the peptides of the present invention.

The present invention further encompasses compositions (including pharmaceutical compositions and food compositions) capable of reducing blood pressure in a subject. Thus, according to a further aspect, the present invention provides for a composition capable of reducing blood pressure in a subject, said composition comprising one or more peptides comprising an amino acid sequence of SEQ ID NO. 1 to SEQ ID NO 28. In aspects, the compositions of the present invention have oral bioactivity. Thus, according to yet a further aspect, the compositions of the invention include, without limitation, food supplements and pharmaceutical compositions suitable for oral delivery.

In aspects, the compositions of the invention comprise one or more novel peptides of the invention for administration to subjects in a biologically compatible form suitable for administration in vivo and suitable for oral delivery. By "biologically compatible form suitable for administration in vivo" is meant a form of the substance to be administered in which any toxic effects are outweighed by the therapeutic effects. The substances may be administered to any subject, preferably, humans. Administration of a therapeutically active amount of the pharmaceutical compositions of the present invention, or an "effective amount", is defined as an amount effective at dosages and for periods of time, necessary to achieve the desired result of eliciting an immune response in a subject. Suitable administration routes are intramuscular injections, subcutaneous injections, intravenous injections or intraperitoneal injections, oral and intranasal administration.

Acceptable carriers are well known to those skilled in the art and include but are not limited too, for example, sterile saline, lactose, sucrose, calcium phosphate, gelatin, dextrin, agar, pectin, peanut oil, olive oil, sesame oil and deionised water.

Furthermore the composition according to the invention may comprise one or more stabilizers such as but not limited to, for example, carbohydrates including sorbitol, mannitol, starch, sucrose, dextrin and glucose, proteins such as albumin or casein, and buffers like alkaline phosphates. Furthermore, the composition of the present invention may comprise one or more adjuvants that enhance the hypotensive properties of the peptides of the invention.

The specific novel peptides derived from yellow pea were identified to inhibit or reduce renin activity. The invention also encompasses therapeutic strategies that involve administering one or more of the novel peptides of the invention to a subject in need. These methods may be used in combination with other known therapies for treating conditions and diseases related to high blood pressure or disturbances of cardiac function such as hypertension, cardio vascular disease and chronic kidney disease. The term "subject" as used in this document includes all members of the animal kingdom, including mammals, preferably humans.

The invention also encompasses therapeutic strategies that involve targeting the RAS pathway to down-regulate blood pressure in a subject. These methods may be used in combination with other known therapies for reducing blood pressure in a subject.

In humans, high blood pressure is involved in many diseases, such as cardiovascular disease and chronic kidney disease. As such, the instant invention also encompasses methods for the treatment of cardiovascular disease and chronic kidney disease in a subject comprising the administration to the subject of a therapeutic composition comprising one or more of the peptides of the invention.

The peptides of the invention may be labeled with a label to facilitate their detection in a variety of assays as is understood by one of skill in the art. Such labels may include but are not limited to radioactive label and fluourescent label. The peptides of the invention may be provided with a carrier such as for example couple to bovine serum albumin (BSA) or keyhole limpet haemocyanin. The peptides may be covalently or non-covalently coupled to a solid carrier such as a microsphere of gold or polystyrene, a slide, chip or to a wall of a microtitre plate. The peptide may be labeled directly or indirectly with a label selected from but not limited to biotin, fluorescin and an enzyme such as horseradish peroxidase.

The above disclosure generally describes the present invention. A more complete understanding can be obtained by reference to the following specific Examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Chemicals

Pea protein isolate (85% protein content) from Pisum sativum L. was a gift from Parrheim Foods (Portage La Prairie, Manitoba. Canada). Purified human recombinant renin was purchased from Cayman Chemical (13.29 U/mg, Ann Arbor, Mich., USA). The enzyme was supplied in 100 mM sodium acetate buffer, pH 4.2 with dry ice. Recombinant enzyme was expressed in HEK cells as the prorenin, and then was activated using trypsin and purified using peptide affinity chromatography. The purity is more than 99% estimated by SDS-PAGE, with a molecular weight of 40 kDa. Renin substrate 1 (Arg-Glu(EDANS)-Ile-His-Pro-Phe-His-Leu-Val-Ile-His-Thr-Lys(dabcyl)-Arg) was purchased from Molecular Probes, Inc. (Eugene, Oreg., USA). Purified rabbit lung angiotensin I-converting enzyme (ACE), thermolysin (Type X, Bacillus thermoproteolyticus rokko, 39 units/mg solid), hippuryl-histidyl-leucine (HHL), and hippuric acid (HA) were purchased from Sigma (St Louis, Mo.). HPLC-grade acetonitrile was purchased from Fisher Scientific (Pittsburgh, Pa.), trifluoroacetic acid (TFA) was obtained from Fluka (Buchs, Switzerland). HPLC-grade water generated by Milli-Q system (Millipore, Bedford, Mass., USA) was used for the preparation of the HPLC mobile phase: all other chemicals were of reagent grade and obtained from Sigma (St Louis, Mo.).

Example 2

Hydrolyzed Pea Protein

Pea protein hydrolysate was prepared in a 800 mL reactor with temperature and pH control devices. Pea protein isolate (80% protein content) was dispersed in distilled water to obtain a 6.0% (w/v) protein slurry. After the slurry was heated to 55° C. and pH was adjusted to 8.0, thermolysin was then added to initiate the hydrolysis at a ratio of 0.5% (on the basis of protein weight, w/w). The temperature of the slurry was maintained at constant value for 3 h while pH 8.0 was maintained by addition of solid sodium hydroxide pellets when necessary. The hydrolysis was stopped by heating at 95° C. for 15 min. The hydrolysate was centrifuged at 10,000×g for 25 min. The clear supernatant was further passed through a cut-off molecular weight 3000 Da ultrafiltration membrane (Sartorius Co., Germany), the resulting permeate was collected, and freeze-dried for further use. Protein content of the hydrolysate was determined to be approx. 85%, while peptide yield was approx. 30% (based on initial weight of protein in the protein isolate).

Example 3

Separation and Identification of Active Fractions of Pea Protein Hydrolysate Bioactive pea hydrolysate is produced by hydrolysis of pea protein isolate with food grade enzyme (thermolysin) followed by centrifugation to recover soluble peptides in the supernatant. The supernatant is passed through a 3 kDa ultrafiltration membrane and the permeate freeze-dried as the bioactive pea protein hydrolysate. The permeate is fractionated by preparative reverse-phase HPLC to yield renin-inhibitory fractions. The active fractions are separated by gel filtration followed by a second round of HPLC using reverse-phase column. HPLC elution is carried out with a linear gradient from solvent A (0.1% trifluoroacetic acid. TFA in water) to solvent B (0.1°/o TFA in acetonitrile) for 60 min at a flow rate that is optimized (at least 5 ml/min); absorbance is detected at 214 nm and pooled fractions collected. Solvents are removed from each pooled fraction in a rotary evaporator and the sample freeze-dried. Purity of peaks are confirmed by analyzing each fraction in a mass spectrometer. Amino acid sequence of the purified peptides are determined using ultra-performance liquid chromatography-tandem mass spectrometer according to established procedures. Two peptide fractions, T4 and T5, from ion exchange chromatography showed promising renin inhibiting activity of 31.0% and 40.1%, respectively at the concentration of 2.5 mg/mL (FIG. 1). Other fractions showed low or no renin inhibiting activity. Since renin is a highly specific enzyme, it is more difficult to obtain potent renin inhibiting peptides from food proteins, compared with ACE inhibiting peptides, an enzyme lacking of specificity. However, our results indicated that specific hydrolyzed peptides from proteins could also inhibit the renin.

Peptide identification was performed on a matrix-assisted laser desorption/ionization (MALDI) coupled with a tandem quadrupole time-of-light (QqTOF) mass spectrometer (commercial model sold as QSTAR by Applied Biosystems/MDS Sciex, Foster City, Calif., USA). Detailed description of the instrument and methodology was published by Loboda. Krutchinsky, Bromirski, Ens and Standing [2002]. Peptide fractions were dissolved by water containing 1.0% TFA, and then introduced on the tip of a MALDI probe for MALDI-MS analysis.

In this instrument, ions are produced by irradiation of the sample with photon pulses from 20 Hz nitrogen laser (VCL 337ND; Spectra-Physics, Mountain View, Calif., USA) with 300 mJ energy per pulse. Orthogonal injection of ions from the quadrupole into the TOF section normally produces a mass resolving power of 10 000 FWHM, and accuracy within a few mDa in the TOF spectra in MS anode. Ions are detected by a microchannel plate detector with a four-segment anode. Data are acquired using pulse-counting four segment methods with a time-to-digital converter (TDCx4, Ion-Werks, Houston, Tex., USA).

Molecular mass distribution of the peptides was determined by size-exclusion chromatography on a Superdex Peptide 10/300 GL column (Amershambiotech, Pharmacia Biotech, Uppsala, Sweden) using an AKTA purifier (Amershambiotech, Pharmacia Biotech, Uppsala, Sweden). The column has the ability of separating molecules of 100-7000. The column was equilibrated and eluted with 20 μM phosphate buffer (pH 7.2) containing 0.25 M NaCl in isocratic mode, at a flow rate of 0.5 ml/min. The eluate was monitored at 214 nm. A protein standard mixture (cytochrome C(Mr, 12500), aprotinin (Mr, 6512), Substance P(Mr, 1348), cytidine (Mr 246) and Glycine (Mr, 75)) was used to establish standard curve. Samples were prepared at a concentration of 3 mg/mL and injected at a volume of 30 L.

Figure 2:
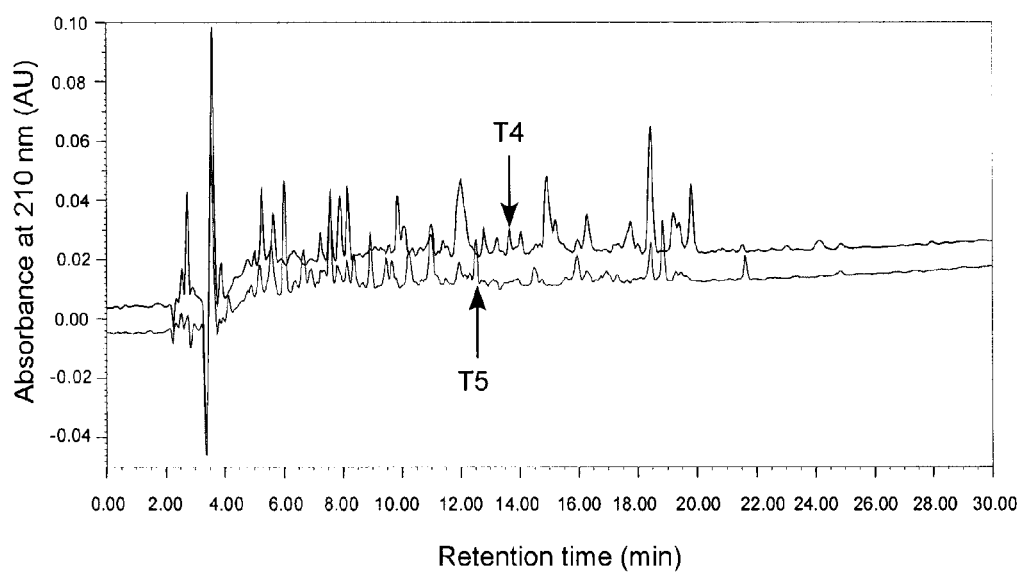
FIG. 2 illustrates HPLC peptide profile of T4 and T5 peptide fractions
Figure 3:
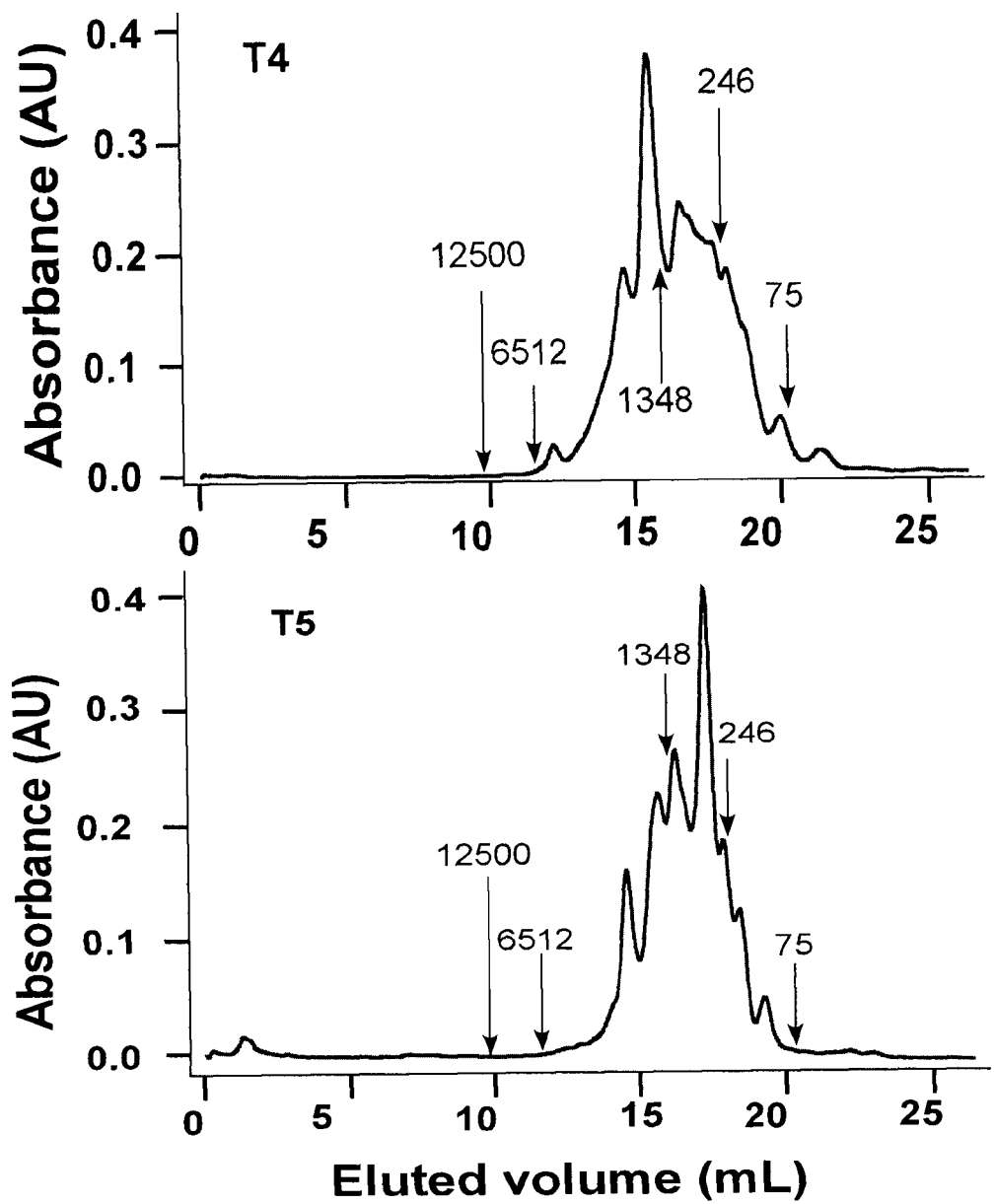
FIG. 3 illustrates the molecular size profile of T4 and T5 peptide fractions
Figure 4:
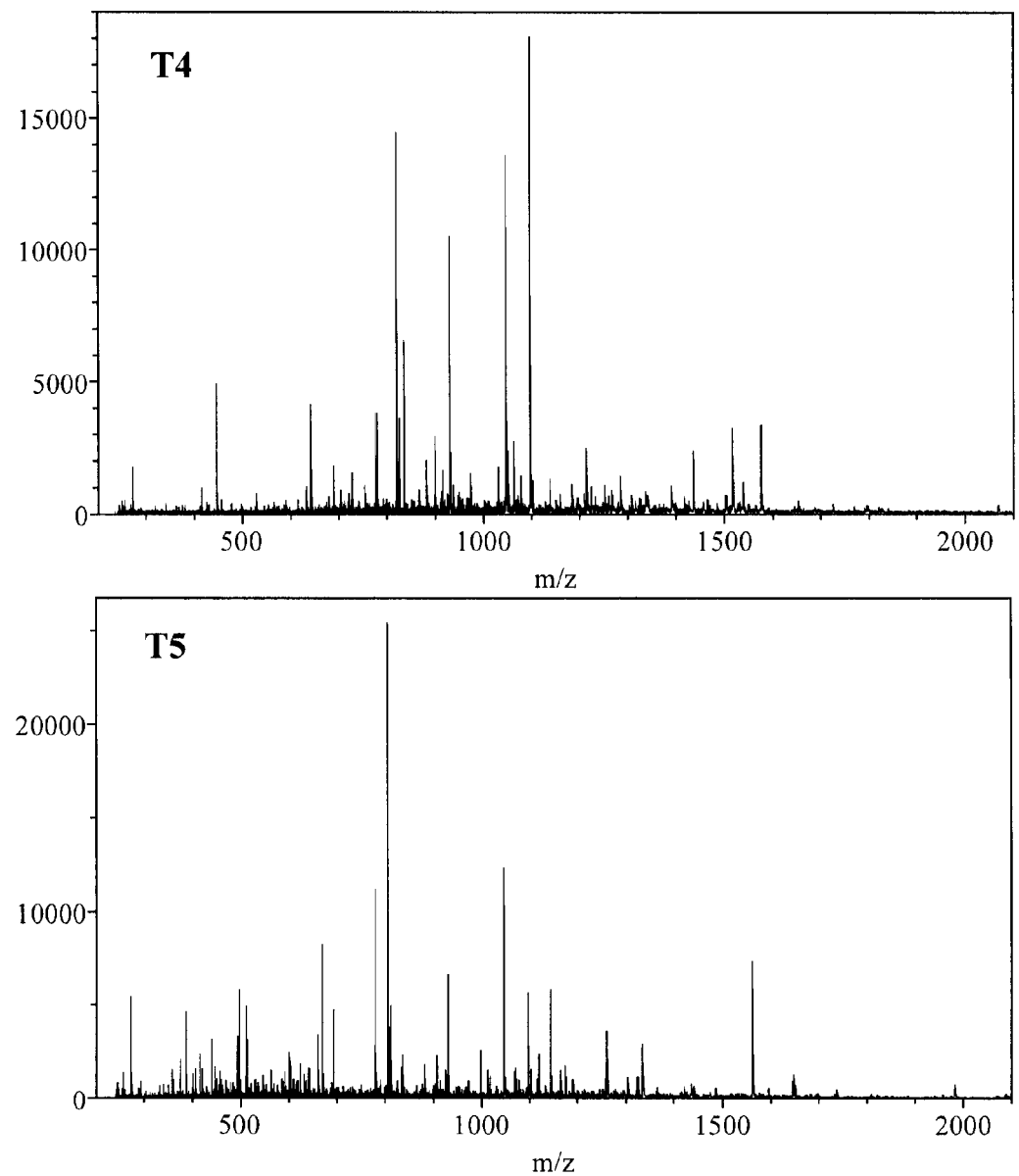
FIG. 4 illustrates the mass spectrometer profile of T4 and T5 peptide fractions.

FIG. 2 shows the HPLC profile of the T4 and T5 peptide fractions obtained from ion exchange chromatography. Different peaks were observed between these two fractions, indicating that different peptide sequences are present in these two fractions. Molecular weight profile of these two fractions were determined by Superdex Peptide gel chromatography and results are shown in FIG. 3. The results showed that peptide fractions of T4 and T5 contained mainly short peptides (FIG. 3), of which 81.9% and 87.1% were less than 1000 Dalton, respectively. Short-chain peptides were reported to be able to be absorbed by intestinal enterocytes and transfer across the capillary wall to blood, and thus leading to a biological activity at the target site (Robert et al 1999). Mass spectrometry can accurately display both the peptide composition and molecular weight (FIG. 4). The majority peptides in T4 fraction showed molecular weight ranging from 600 to 1600 Dalton, the most abundant peptides fell in the molecular weight ranging from 800 to 1200 Dalton. There were more peptides in lower molecular weight range in T5 fraction than that of T4 fraction. In both fractions, there were very few peptides that showed molecular weight greater than 1500 Dalton (FIG. 4). The results clearly indicated that the presence of different peptides in these two fractions are involved in renin and ACE inhibiting activities.

Example 4

Inhibition of Human Recombinant Renin Activity

Renin inhibitory activity assays were carried out on a Shimadzu RF 1501 spectrofluorometer equipped with thermostated cell holder according to the method of Wang, Chung, Holzman, & Krafft (1993) with some modifications (FIG. 5 and Table 1). The following instrumental parameters were used: excitation wavelength, 340 nm; emission wavelength, 490 nm; excitation and emission bandwidth, 10 nm. A standard 2 mL, 1 cm pathlength cuvettes containing 1 mL of buffer (or 1 mL varied peptide concentrations) and 1 mL of 2.5 µM substrate, was equilibrated at 37° C. for 5 min to gain thermal equilibrium. A 15 µL of renin (0.4 µg renin) was then added to the cuvette to initiate the reaction. The time dependent increase of fluorescence intensity was monitored for 5 min. The initial reaction velocity, expressed in arbitrary fluorescence units per minute (FU/min), was calculated by least-squares analysis of the initial phase of the reaction. The renin inhibiting activity of the peptide fractions and the individual peptides within are described in Table 1.

TABLE 1

| PEPTIDE(S) | RENIN INHIBITION % |
| --- | --- |
| SEQ ID NO. 1 | 49.11 |
| SEQ ID NO. 2 | 28.78 |
| SEQ ID NO. 3 | 22.36 |
| SEQ ID NO. 4 | 33.97 |
| SEQ ID NO. 5 | 25.36 |
| SEQ ID NO. 6 | 12.04 |
| SEQ ID NO. 7 | 15.90 |
| SEQ ID NO. 8 | 15.13 |
| SEQ ID NO. 9 | 20.40 |
| SEQ ID NO. 10 | 6.35 |
| SEQ ID NO. 11 | 8.92 |
| SEQ ID NO. 12 | 8.64 |
| SEQ ID NO. 13 | 4.85 |
| SEQ ID NO. 14 | 15.39 |
| SEQ ID NO. 15 | 43.37 |
| SEQ ID NO. 16 | 21.24 |
| SEQ ID NO. 17 | 57.53 |
| SEQ ID NO. 18 | 9.30 |
| SEQ ID NO. 19 | 22.19 |
| SEQ ID NO. 20 | 23.97 |
| SEQ ID NO. 21 | 36.02 |
| SEQ ID NO. 22 | 43.55 |
| SEQ ID NO. 23 | 76.16 |
| SEQ ID NO. 24 | 28.03 |
| SEQ ID NO. 25 | 6.73 |
| SEQ ID NO. 26 | 32.43 |
| SEQ ID NO. 27 | 69.18 |
| SEQ ID NO. 28 | 37.15 |
| FRACTION T4 | 31.00 |
| FRACTION T5 | 40.10 |

Figure 6:
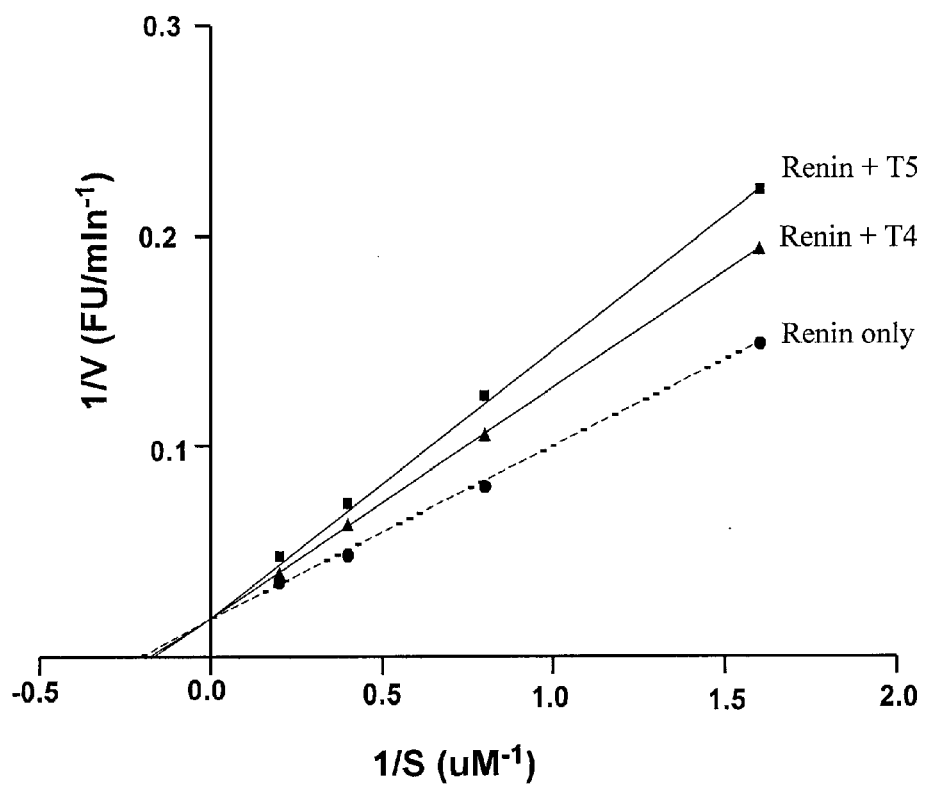
FIG. 6 illustrates the inhibitory patterns displayed by T4 and T5 towards renin.

Renin inhibiting assay was modified from the fluorometric assay developed for renin activity measurement (FIG. 5). In the presence of active peptide fraction, the fluorescence intensity decreased indicating that the renin activity was inhibited by the addition of peptide fraction. Based on Lineweaver-Burk plots (FIG. 6), T4 and T5 fractions appeared to be competitive inhibitors. To date, most reported renin inhibitors are competitive inhibitors (Parikh and Cuatrecasas, 1973; Poulsen et al 1976). The Michaelis-Menten constant (Km) in our study is 3.8 µM for human recombinant renin in the absence of peptide fractions. This value is close to the reported KM of 3.6 µM using the same source of renin and substrate under similar assay conditions (Holzman et al 1991). However, Km of human recombinant renin was also reported to be 1.62 µM (Toshihisa et al., 1992), or 1.25 µM in purified human renal renin acting on pure human plasma angiotensingen at pH 5.7 (Cumin et al., 1987), 1.54 µM at pH 6.5 (Slater and Strout 1981). The Km value for the reaction between renin and substrate also depends on pH, ionic strength, the medium and the assay procedure used (Poulsen et al., 1976). The Michaelis-Menten constants were increased to 6.3 and 6.1 µM, respectively in the presence of peptide fractions of T4 and T5, indicating decreased binding ability between renin and substrate because of the presence of competitive peptide inhibitors.

Example 5

In Vivo Animal Model Experiments in Polycystic Kidney Disease Rats

SPRD-cy (this is a Sprague-Dawley rat with the cy mutation that causes the rat to develop polycystic kidney disease and severe hypertension). There were 13 heterozygous male rats per group. The groups consisted of groups fed with a casein control diet, isolated pea protein diet, 0.5% yellow pea protein hydrolysate diet (Hydrolysate 5), and 1% yellow pea protein hydrolysate diet (Hydrolysate 10) according Table 2. The heterozygous rats were weaned at 21 days of age and fed the treatment diet for 5 weeks with weekly measurements of blood pressure by the tail cuff method after warming the rats to 37° C. Male rats were used because the disease (kidney cysts formation and hypertension) progresses much faster than in females and effects of nutritional intervention are easier to detect. If they are not sacrificed, the heterozygous male rats will die from kidney failure after about 10 weeks of age, so the experiment was terminated at 8 weeks in accordance with animal ethics regulations. Blood and organs were collected during termination. A mean decrease of 29 mmHg in systolic blood pressure was obtained after two weeks of feeding with the pea protein hydrolysate.

TABLE 2

| Ingredient | Diet Group | | | |
|---|---|---|---|---|
| | Casein | Pea protein isolate | Hydrolysate 5 | Hydrolysate 10 |
| Corn starch | 37.95% | 37.95% | 37.95% | 37.95% |
| Casein | 20% | | 19.5% | 19% |
| Pea protein isolate | | 20% | | |
| Pea Protein Hydrolysate | | | 0.5% | 1% |
| Dex cornstarch | 13.2% | 13.2% | 13.2% | 13.2% |
| Sucrose | 10% | 10% | 10% | 10% |
| Corn oil | 7% | 7% | 7% | 7% |
| Fiber | 5% | 5% | 5% | 5% |
| Min. mix | 3.5% | 3.5% | 3.5% | 3.5% |
| Vit. mix. | 1% | 1% | 1% | 1% |
| L-c V s | 0.3% | 0.3% | 0.3% | 0.3% |
| Choline bitart | 0.25% | 0.25% | 0.25% | 0.25% |
| TBHQ | 0.0014% | 0.0014% | 0.0014% | 0.0014% |
| Total | 100% | 100% | 100% | 100% |

Figure 7:
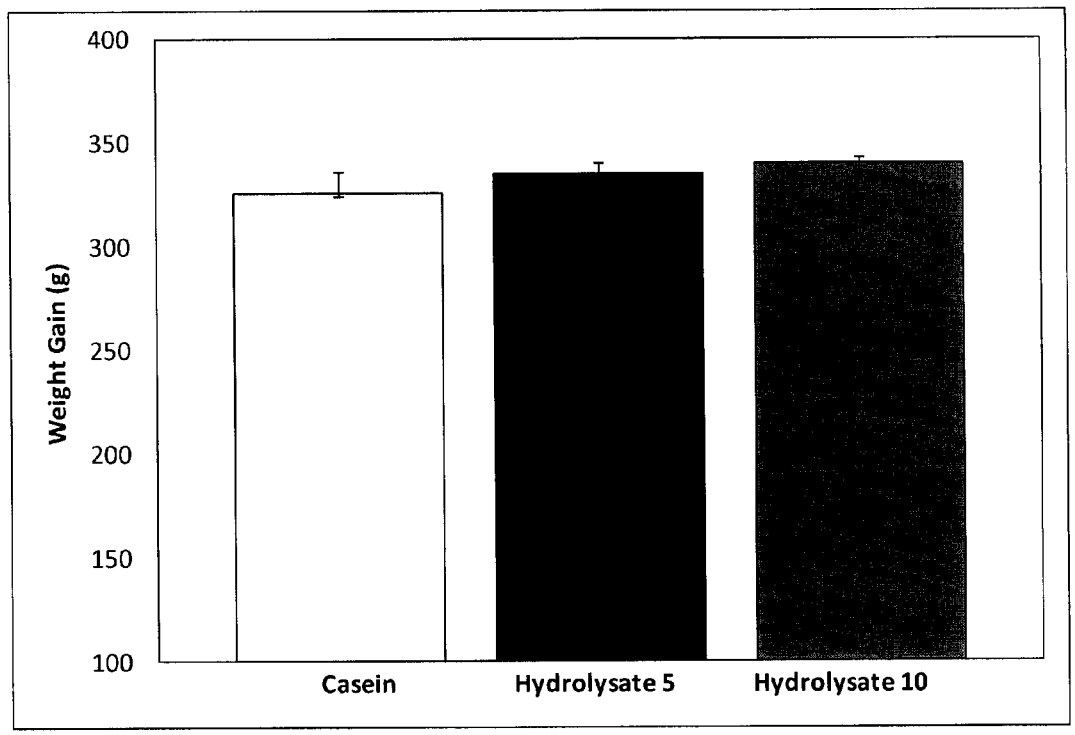
FIG. 7 illustrates weight gain by polycystic kidney disease (PKD) rats divided into three diet groups: casein, hydolysate 5 which contains 0.5% composition consisting of the active fractions of yellow pea protein hydrolysate and hydrolysate 10 which contains 1.0% composition consisting of the active fractions of yellow pea protein hydrolysate.

There were no differences in the weights of rats from different diet treatments (FIG. 7); therefore, we can conclude that the observed results are not due to changes in weight. As shown in FIG. 8, incorporation of pea protein hydrolysate into the diet led to a decrease in systolic blood pressure of about 29 mmHg from age 6 to 8 weeks when compared to rats fed casein diet only. The decrease in blood pressure is supported by the observed decrease in plasma concentrations of angiotensin II (FIG. 9), which correlated with decrease in systolic blood pressure. Urine production by the rats was also significantly improved as a result of incorporation of the pea protein hydrolysate into the diet (FIG. 10), which indicates increased ability of the kidneys to filter blood.

Example 5

In Vivo Animal Model Experiments in Spontaneously Hypertensive Rats

Animal experiments were carried out following the Canadian Council on Animal Care ethics guidelines with a protocol approved by the University of Manitoba Animal Protocol and Management Review Committee. The spontaneously hypertensive rats (SHR) were kept in the Animal Housing Facility at the Richardson Centre for Functional Foods and Nutraceuticals, University of Manitoba under a 12-hr day and night cycle at 21° C. and were fed a regular chow diet and tap water, ad libitum. The SHR were divided into 6 groups that received the following treatments (dissolved in phosphate buffered saline, pH 7.2): ADMFPF (SEQ ID NO. 23) peptide (n=6), WMP (SEQ ID NO. 15) peptide (n=6), captopril (positive control, n=6), saline (negative control, n=6). The peptides (each at 30 mg/kg body weight, BW) and captopril (3 mg/kg BW) were administered to the SHR by oral gavage followed by measurement of systolic blood pressure (SBP) at 2, 4, 6, 8 and 24 hr by the tail-cuff method in slightly anesthesized rats. Prior to sample administration, the baseline (time zero) SBP was determined. In order to mitigate the blood pressure (BP) depression effect of isofluorane, the gas flow was optimized such that rats became conscious usually within 3-4 min after removal from the chamber, which provided enough time to perform the blood pressure measurement. Rats were first anesthesized in a chamber (maintained at about 40° C.) with 4% isofluorane for 4 min. They were then removed from the isofluorane chamber and tail-cuff measurement of blood pressure performed in the unconscious state. The change in SBP ($\Delta$SBP, mmHg) was determined by subtracting the data for the different time points from their respective baseline data.

The Applicant shows in FIG. 16 that the two peptides ADMFPF (SEQ ID NO. 23) and WMP (SEQ ID NO. 15) showed hypotensive activities comparable to captopril (a commercial ACE-inhibitory drug), especially in terms of duration of effect over a 24 hr period. The WMP, which has less renin-inhibitory activity than ADMFPF showed initial higher hypotensive effects especially up to 8 hours after oral administration. However, the more active renin inhibitor (ADMFPF) sustained the hypotensive effect (−25 mmHg) longer than WMP (−14 mmHg) as shown by the 24 hour systolic blood pressure. Captopril was also less effective after 24 hour when compared to ADMFPF. The results confirm the hypothesis that renin-inhibitory peptides could provide better hypotensive effects than ACE-inhibitory compounds. The test conducted on the identified two peptides noted above is applicable to the remaining 24 peptides showing renin inhibiting activity identified herein.

Example 6

RNA Isolation

Organ tissue (heart and kidneys) of rats was mixed with 4 ml of TRIZOL reagent and homogenized. The homogenate was transferred into four 1 ml Eppendorf tubes and 0.2 ml of chloroform was added. The tubes were shaken and then centrifuged at 10,000×g for 15 min at 4° C.; the upper aqueous phase contained the RNA, which was then transferred into a clean Eppendorf tube. A 0.5 ml aliquot of isopropanol was added to the transferred aqueous phase and allowed to stand at room temperature for 10 min followed by centrifugation at 10,000×g for 10 min at 4° C. The supernatant was discarded and the pellet washed with 1 ml of 75% ethanol, vortexed and centrifuged at 5,000×g for 5 min at 4° C. The washed RNA was slightly air-dried and concentration determined by spectrophotometry. RT-PCR was carried out using the Bio-Rad kit.

Primers used for amplification were synthesized as follows:

```
GAPDH:     CAT GAC AAC TTT GGC ATC GT (forward)
           GGA TGC AGG GAT GAT GTT CT (reverse)

Renin:     TTC AGG AAC GAT GAC CTG TG (forward)
           GAA CCC GAT GCG ATT GTT AT (reverse)

ACE:       CAT GTC ACT TTC TGC AGC TAC C (forward)
           ACC ATC CAC CTC CAC TTC TCT A (reverse)

AT-I R:    GGA AAC AGC TTG GTG GTG AT (forward)
           ACA TAG GTG ATT GCC GAA GG (reverse)

COX-1:     TCT GAT GCT CTT CTC CAC GA (forward)
           TCC TCC TTC AGC AAG TCA CA (reverse)

COX-2:     AGT GAT CGA AGA CTA CGT GCA A (forward)
           CTG ATA CTG GAA CTG CTG GTT G (reverse)
```

Figure 12:
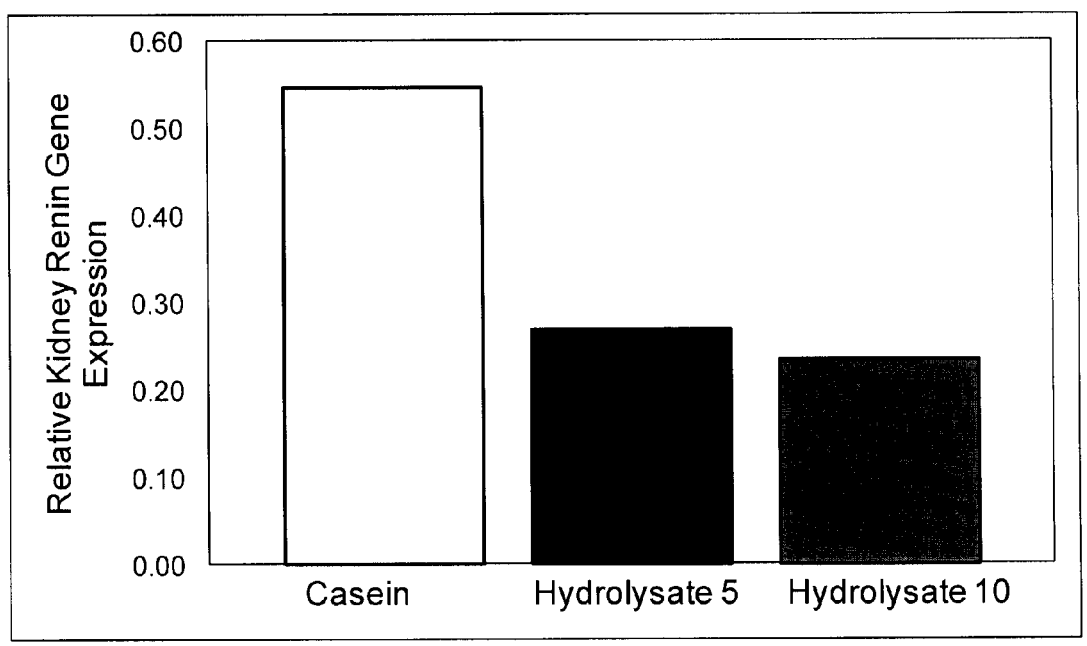
FIG. 12 illustrates the effect of diet containing yellow pea seed protein hydrolysate in kidney renin gene expression in PKD rats.
Figure 13:
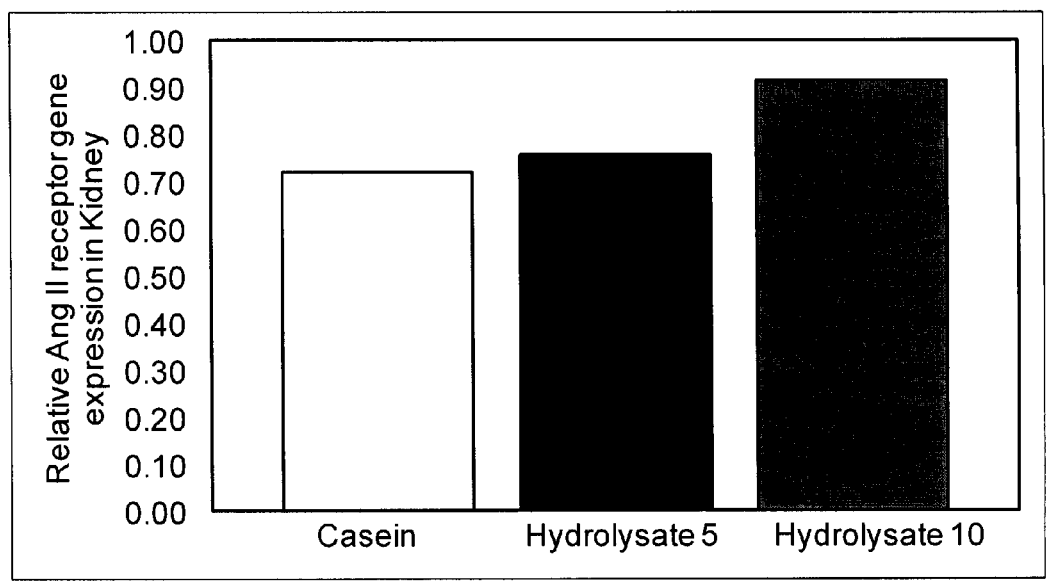
FIG. 13 illustrates the effect of diet containing yellow pea seed protein hydrolysate on kidney angiotensin II receptor gene expression in PKD rats.
Figure 14:
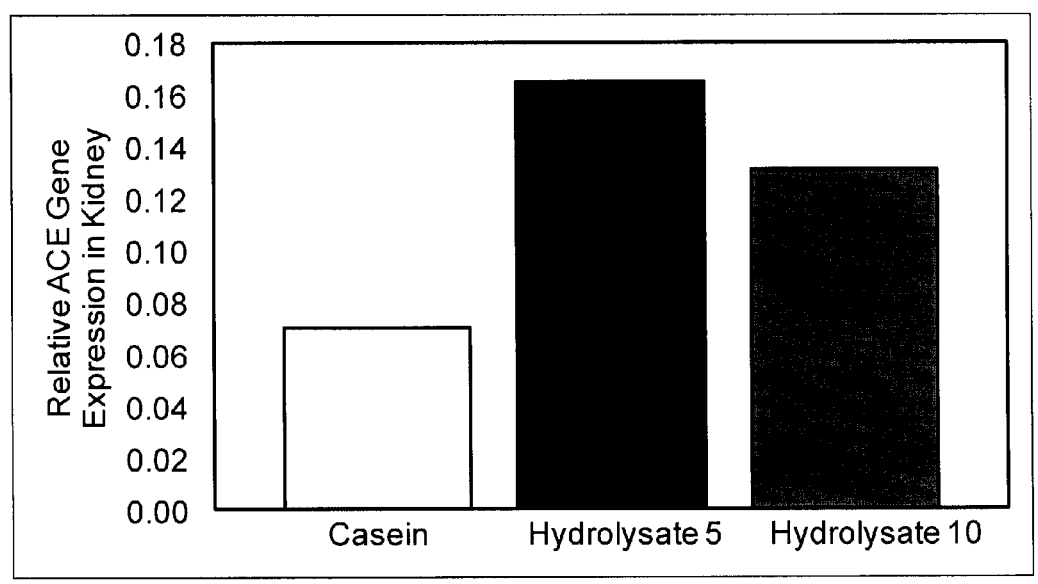
FIG. 14 illustrates the effect of diet containing yellow pea seed protein hydrolysate on kidney ACE gene expression in PKD rats.

FIG. 11 shows that at the lower level of 0.5% incorporation of pea protein hydrolysate, there was a significant decrease in the amount of renin mRNA present in the heart. Renin gene expression was significantly decreased by the two levels of pea protein hydrolysate (FIG. 12), which is correlated with the observed decrease in systolic blood pressure of the rats. In contrast there was no significant effect of pea protein hydrolysate on the mRNA levels for angiotensin II receptor (FIG. 13), which indicates that the observed decreases in blood pressure are not related to the level of cellular receptors for angiotensin II uptake. ACE mRNA levels were actually increased by the pea protein hydrolysate when compared to the casein only diet. Thus the observed decreases in angiotensin II levels could not have been due to the changes in level of ACE. Cyclooxygenase-1 (COX-1) and cyclooxygenase-2 (COX-2) mRNA levels were significantly increased by the pea protein hydrolysate. COX-1 and COX-2 are believed to produce eicosanoids that enhance blood flow during kidney disease. Therefore, the higher levels of COX-1 and COX-2 associated with consumption of the pea protein hydrolysate could be related with the observed increases in urine production (FIG. 10) as a result of better blood flow within the kidney tissues. These results indicate that the consumption of pea protein hydrolysate by a subject can lead to a reduction of the effects of kidney disease in a subject.

The invention claimed is:

1. A method of treating kidney disease in a subject, comprising administering to the subject a composition comprising an effective amount of a peptide consisting of the amino acid sequence of SEQ ID NO. 23.

2. A method of treating kidney disease in a subject, comprising administering to the subject a composition comprising an effective amount of a peptide consisting of the amino acid sequence of SEQ ID NO. 23, wherein administering the composition to the subject increases urine output.

3. A method of treating kidney disease in a subject, comprising administering to the subject a composition comprising an effective amount of a peptide consisting of the amino acid sequence of SEQ ID NO. 23, wherein administering the composition to the subject lowers blood pressure in the subject.

4. A method of treating kidney disease in a subject, comprising administering to the subject a composition comprising an effective amount of a peptide consisting of the amino acid sequence of SEQ ID NO. 23, wherein administering the composition to the subject inhibits the production of angiotensin II by the kidneys of the subject.

5. A method of treating kidney disease in a subject, comprising administering to the subject a composition comprising an effective amount of a peptide consisting of the amino acid sequence of SEQ NO. 23, wherein administering the composition to the subject reduces expression of messenger ribonucleic acid (mRNA) for renin by the kidneys of the subject.

6. The method of claim 1 wherein the kidney disease is polycystic kidney disease.

7. The method of claim 2 wherein the kidney disease is polycystic kidney disease.

8. The method of claim 3 wherein the kidney disease is polycystic kidney disease.

9. The method of claim 4 wherein the kidney disease is polycystic kidney disease.

10. The method of claim 5 wherein the kidney disease is polycystic kidney disease.

* * * * *